United States Patent
Tsuyuki et al.

(10) Patent No.: US 7,630,472 B2
(45) Date of Patent: Dec. 8, 2009

(54) X-RAY COMPUTED TOMOGRAPHY APPARATUS

(75) Inventors: Masaharu Tsuyuki, Nasushiobara (JP); Takamasa Oota, Abiko (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/461,603

(22) Filed: Aug. 1, 2006

(65) Prior Publication Data

US 2007/0030946 A1 Feb. 8, 2007

(30) Foreign Application Priority Data

Aug. 3, 2005 (JP) ............................. 2005-225537

(51) Int. Cl.
*A61B 6/00* (2006.01)
(52) U.S. Cl. .............................................. 378/8; 378/4
(58) Field of Classification Search ..................... 378/4, 378/8, 93–95, 98.11–98.12, 901
See application file for complete search history.

(56) References Cited

U.S. PATENT DOCUMENTS

| | | | | |
|---|---|---|---|---|
| 5,671,263 | A * | 9/1997 | Ching-Ming | 378/8 |
| 5,832,051 | A * | 11/1998 | Lutz | 378/8 |
| 6,154,516 | A * | 11/2000 | Heuscher et al. | 378/15 |
| 6,243,437 | B1 * | 6/2001 | Hu et al. | 378/8 |
| 6,421,552 | B1 * | 7/2002 | Hsieh | 600/425 |
| 6,434,215 | B1 * | 8/2002 | Cesmeli | 378/8 |
| 6,510,337 | B1 * | 1/2003 | Heuscher et al. | 600/428 |
| 6,535,570 | B2 * | 3/2003 | Stergiopoulos et al. | 378/8 |
| 7,006,593 | B2 * | 2/2006 | Kokubun et al. | 378/8 |
| 7,042,975 | B2 * | 5/2006 | Heuscher | 378/8 |
| 7,212,602 | B2 * | 5/2007 | Tsujii | 378/8 |
| 2002/0131545 | A1 * | 9/2002 | Hsieh | 378/4 |
| 2004/0022365 | A1 * | 2/2004 | Patch | 378/210 |
| 2004/0087853 | A1 * | 5/2004 | Fujisawa | 600/425 |
| 2004/0120446 | A1 * | 6/2004 | Londt et al. | 378/4 |
| 2004/0179644 | A1 | 9/2004 | Tsuyuki | |

OTHER PUBLICATIONS

Taguchi et al., Algorithm for image reconstruction in multi-slice helical CT, Med Phys, 25, 4, Apr. 1998, pp. 550-561.*

* cited by examiner

*Primary Examiner*—Edward J Glick
*Assistant Examiner*—Alexander H Taningco
(74) *Attorney, Agent, or Firm*—Oblon, Spivak, McClelland, Maier & Neustadt, L.L.P.

(57) ABSTRACT

An X-ray computed tomography apparatus includes an X-ray tube which generates X-rays, an X-ray detector which detects X-rays transmitted through a subject to be examined, a mechanism which continuously rotates the X-ray tube and the X-ray detector, a storage unit which stores projection data detected by the X-ray detector, a read unit which reads out projection data sets of parts of a pair spaced apart from each other by 360° from the storage unit, an index generating unit which generates a plurality of indices indicating movement of a heart on the basis of a difference between the projection data sets of the parts of the pair, a cardiac phase determination unit which determines a cardiac phase on the basis of the indices, and a reconstruction unit which reconstructs an image on the basis of a full projection data set corresponding to the determined cardiac phase.

19 Claims, 12 Drawing Sheets

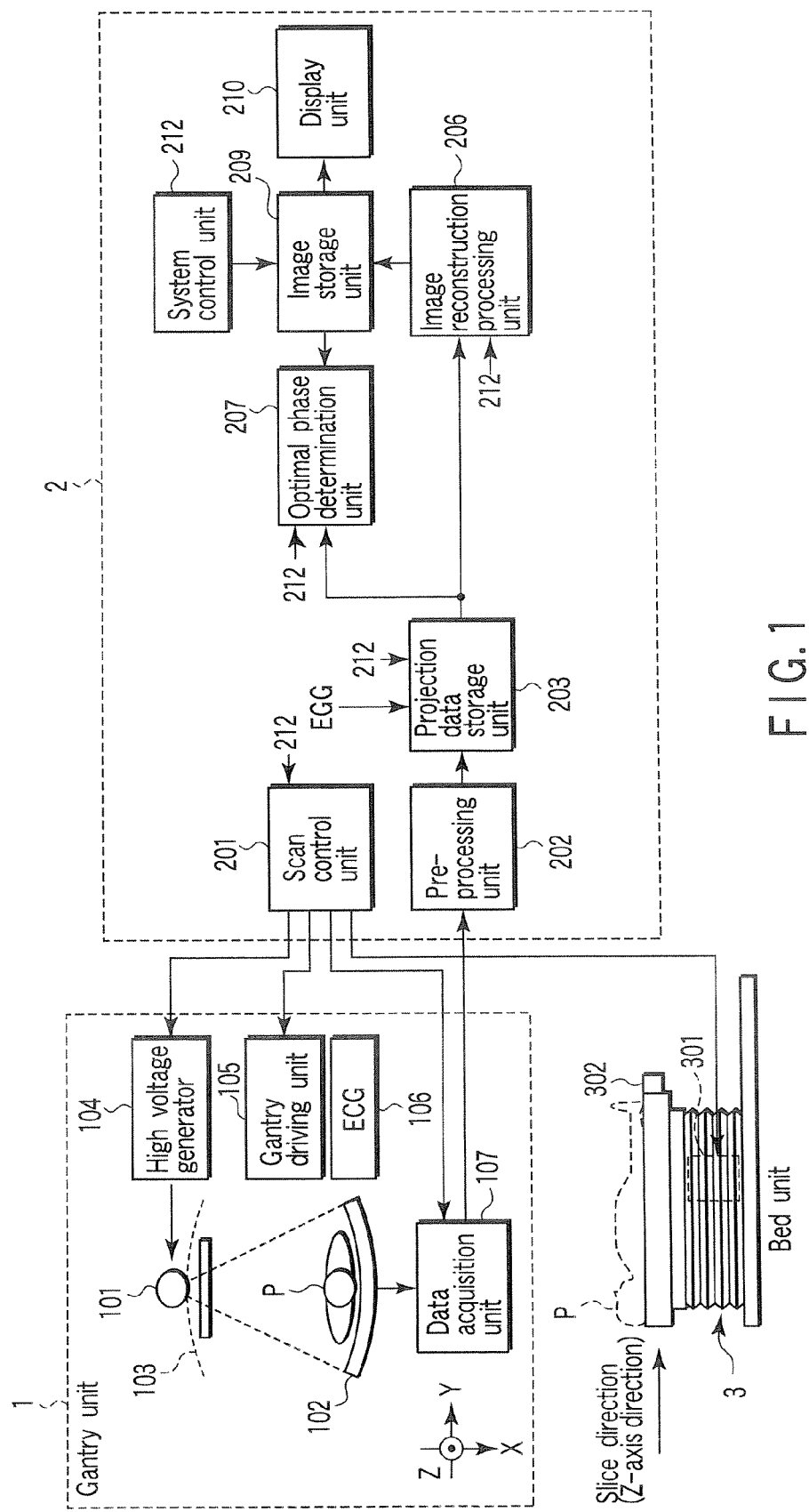
F I G. 1

X-RAY COMPUTED TOMOGRAPHY APPARATUS

CROSS-REFERENCE TO RELATED APPLICATIONS

This application is based upon and claims the benefit of priority from prior Japanese Patent Application No. 2005-225537, filed Aug. 3, 2005, the entire contents of which are incorporated herein by reference.

BACKGROUND OF THE INVENTION

1. Field of the Invention

The present invention relates to an X-ray computed tomography apparatus which scans a subject to be examined with X-rays and reconstructs image data on the basis of obtained projection data using an ECG-gated reconstruction method.

2. Description of the Related Art

An X-ray computed tomography apparatus provides information about a subject to be examined in the form of images on the basis of the intensities of X-rays transmitted through the subject, and plays important roles in many medical activities such as disease diagnosis and medical and operation planning.

In examination of a fast-moving part using an X-ray computed tomography apparatus, and in particular, cardiac examination, one of the important challenges is to improve the time resolution of images. The main means for achieving this challenge include a combination of the half reconstruction method and the ECG-gated reconstruction method. As is known, according to this method, a half projection data set acquired while an X-ray tube rotates about the phase (cardiac phase) of the movement of the heart which is designated by an operator within the range of $180°+\alpha$ (where $\alpha$ is the fan angle of a fan-shaped X-ray beam) is extracted. A full projection data set in a 360° range is generated from the extracted half projection data set by a two-dimensional filter (to be simply referred to as a filter hereinafter) using a so-called Parker's two-dimensional weighting factor map. Image data is reconstructed from the full projection data in the 360° range. Note that a cardiac phase is the position of the period obtained by normalizing the indefinite period from an R wave to the next R wave with 0 to 100%, which is expressed in %.

In CT, the time required for a rotation of 360° or the time required for a rotation of $(180°+\alpha)$ in half reconstruction, is restricted as a substantial time resolution in terms of the principle of image reconstruction. Therefore, image quality inevitably deteriorates due to blurring or the like originating from the magnitude of the pulsation of the heart within this substantial time resolution.

In many cases, it has been difficult to designate an optimal cardiac phase, i.e., a cardiac phase exhibiting the least movement of the heart in a time width which corresponds to the substantial time resolution and is centered on the cardiac phase (see Jpn. Pat. Appln. KOKAI Publication No. 2004-275440).

BRIEF SUMMARY OF THE INVENTION

It is an object of the present invention to specify an optimal cardiac phase for ECG-gated reconstruction in an X-ray computed tomography apparatus which reconstructs, using an ECG-gated reconstruction method, image data based on data obtained by scanning a subject to be examined.

According to an aspect of the present invention, there is provided an X-ray computed tomography apparatus comprising an X-ray tube which generates X-rays, an X-ray detector which detects X-rays transmitted through a subject to be examined, a mechanism which continuously rotates the X-ray tube and the X-ray detector, a storage unit which stores projection data detected by the X-ray detector, a read unit which reads out projection data sets of parts of a pair spaced apart from each other by 360° from the storage unit, an index generating unit which generates a plurality of indices indicating movement of a heart on the basis of a difference between the projection data sets of the parts of the pair, a cardiac phase determination unit which determines a cardiac phase on the basis of the indices, and a reconstruction unit which reconstructs an image on the basis of a full projection data set corresponding to the determined cardiac phase.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the arrangement of an X-ray computed tomography apparatus according to an embodiment of the present invention;

DETAILED DESCRIPTION OF THE INVENTION

Figure 2:
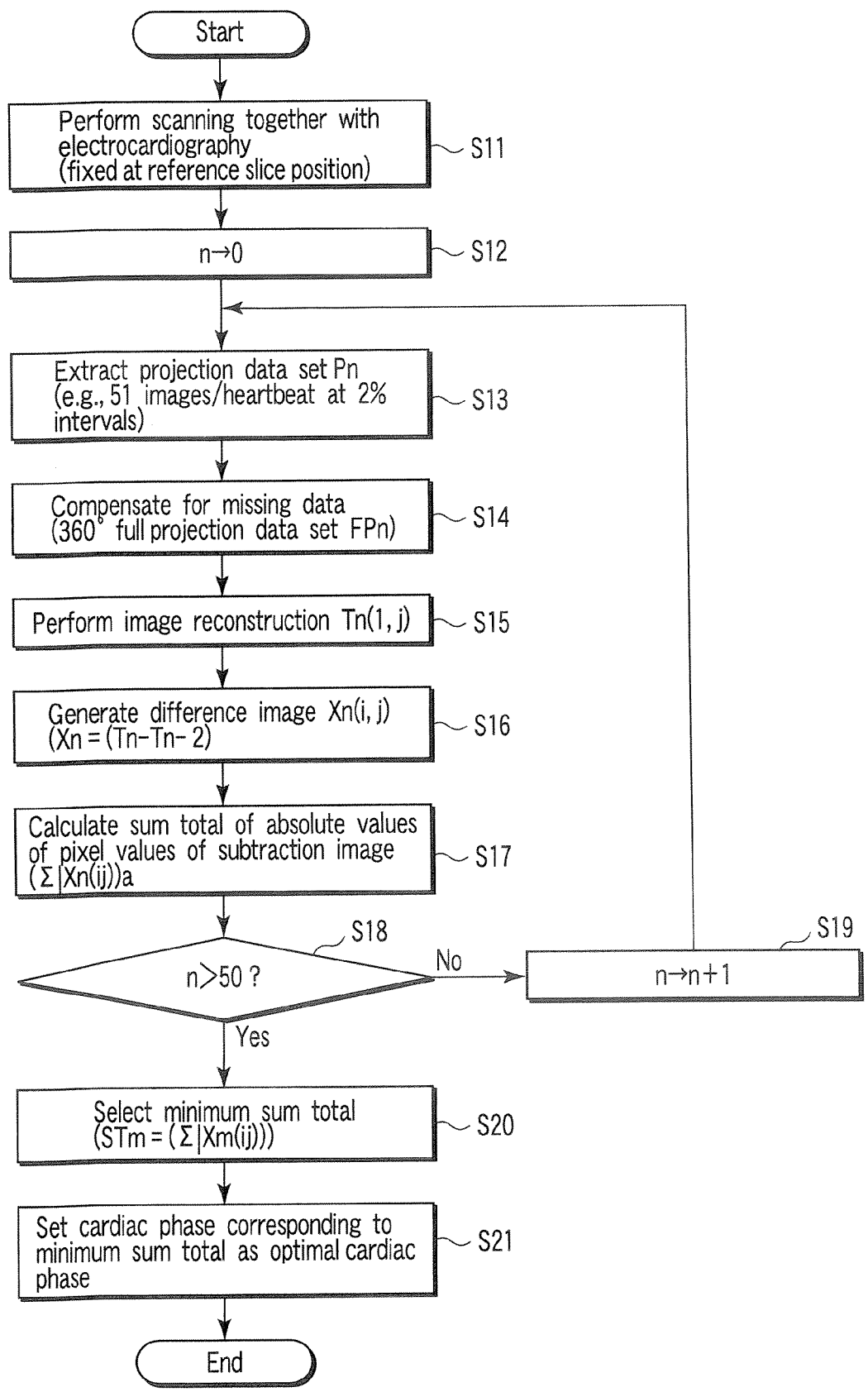
FIG. 2 is a flowchart showing an optimal cardiac phase determination sequence based on the first mode (image differences) in this embodiment.

An embodiment of an X-ray computed tomography apparatus according to the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements are arrayed in the form of a ring, and only an X-ray tube rotates around a subject to be examined. The present invention can be applied to either type. In this case, the rotate/rotate type, which is currently the mainstream, will be exemplified. In order to reconstruct one-slice tomogram data, a full projection data set (full reconstruction method) corresponding to one rotation around a subject to be examined, i.e., about 360°, is required, or a half projection data set corresponding to 180°+α (α: fan angle) is required in the half reconstruction method. This embodiment uses the half reconstruction method effective for imaging of the heart with fast movement or the like. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomography apparatus having a plurality of pairs of X-ray tubes and X-ray detectors mounted on a rotating ring, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

FIG. 1 shows the arrangement of an X-ray computed tomography apparatus according to this embodiment. The X-ray computed tomography apparatus includes a gantry unit 1 designed to acquire projection data associated with a subject to be examined. The gantry unit 1 includes an X-ray tube 101 and an X-ray detector 102. As the X-ray detector 102, a 64-row multi-slice type detector (multi-row type detector) which covers the heart area is typically used. However, a single-slice type detector (single-row detector) may be used as the X-ray detector 102.

The X-ray tube 101 and the X-ray detector 102 are mounted on a ring-shaped rotating frame 103 which is rotated/driven by a gantry driving unit 105. In this case, the rotation axis of the rotating frame 103 is defined as the Z-axis. In a rotating coordinate system centered on the Z-axis, an axis perpendicular to the Z-axis which connects the focal point of the X-ray tube 101 and the center of the detection surface of the X-ray detector 102 is defined as the X-axis. The Y-axis is perpendicular to both the Z-axis and the X-axis.

An opening portion is formed in both the central portion of the rotating frame 103 and the housing. In imaging operation, a subject P placed on a top 302 of a couch unit 3 is inserted into the opening portion. In order to detect an electrocardiogram of the subject P, an electrocardiograph 106 is mounted on the subject P. Note that the electrocardiograph 106 is mounted as a unit for measuring a biometrical signal from the subject P.

A high voltage generator 104 applies a tube voltage (high voltage) between the cathode and the anode of the X-ray tube 101. The high voltage generator 104 also supplies a filament current to the filament of the X-ray tube 101. X-rays are generated from the X-ray tube 101 by the application of the tube voltage and the supply of the filament current.

The X-ray detector 102 has a plurality of X-ray detection elements, each having a 0.5 mm×0.5 mm square light-receiving surface. For example, 916X-ray detection elements are arranged in the channel direction (approximated to the Y-axis). For example, 64 element arrays arranged side by side in the slice direction.

A data acquiring unit 107 generally called a DAS (Data Acquisition System) converts a signal output from the X-ray detector 102 for each channel into a voltage signal, amplifies it, and further converts it into a digital signal. This data (also called pure raw data) is supplied to a computer body 2 placed outside the gantry. A pre-processing unit 202 of the computer body 2 performs pre-processing such as sensitivity correction for the pure raw data output from the data acquisition unit 107. The pre-processed pure raw data is called raw data or projection data. In this case, such data will be genetically called projection data.

Projection data is stored in a projection data storage unit 203, together with the electrocardiogram data obtained by the electrocardiograph 106, while codes representing a view representing the rotation angle of the X-ray tube 101 at the time of data acquisition, a row umber, and the position of the top 302 are associated with each other. Although this embodiment will exemplify a case wherein projection data obtained by helical scanning is processed, the present invention can be applied to dynamic scanning.

In addition to the pre-processing unit 202 and the projection data storage unit 203, the computer body 2 includes a scan control unit 201, image reconstruction processing unit 206, optimal phase determination unit 207, image storage unit 209, display unit 210, and system control unit 212. The image reconstruction processing unit 206 performs ECG-gated reconstruction on the basis of the electrocardiographic information measured by the electrocardiograph 106 and the projection data detected by the X-ray detector 102. The image reconstruction processing unit 206 combines projection data of a plurality of heartbeats corresponding to a set cardiac phase to performed reconstruction, thereby displaying an image corresponding to the cardiac phase.

The optimal phase determination unit 207 is an important constituent element in this embodiment. The details of this unit will be described below. In practice, the optimal phase determination unit 207 is provided as a program for the X-ray computed tomography apparatus to make the computer implement various means to be described later with reference to the flowcharts. The optimal phase determination unit 207 operates in the first or second mode which can be selected by the operator through an operation input unit (not shown) such as a mouse or keyboard, and specifies an optimal position, i.e., a cardiac phase exhibiting the least movement of the heart (pulsation) or a phase most approximated to the cardiac phase. In the first mode, a reconstructed image is handled to specify an optimal phase. In the second mode, projection data before reconstruction is handled to specify an optimal phase. Note that a phase is described with "%" notation which is a typical notation. However, msec (millisecond) notation based on an R wave may be used.

The first and second modes will be sequentially described blow.

FIG. 2 shows a series of operations for determining an optimal phase in the first mode. First of all, a reference slice position is designated on the scanogram shown in FIG. 4A so as to cross the heart in accordance with a user instruction under the control of the system control unit 212. The scanogram can be substituted by an MPR image or the image acquired by another imaging apparatus. At the designated slice position, scanning is executed upon acquisition of an electrocardiographic waveform (S11). With this operation, projection data is acquired throughout at least one heartbeat period, and stored in the projection data storage unit 203. When the scanning operation is complete, the operation of the optimal phase determination unit 207 is started.

First of all, a variable n for identifying a cardiac phase is initialized to 1 (S12). Obviously, the variable n is a variable set for the sake of convenience. In practice, it is completely arbitrary how this variable is implemented on a program. For example, if a cardiac cycle is divided at 2% intervals, n becomes 0, 1, 2, 3, . . . , 49, 50, they respectively correspond to cardiac phases of 0%, 2%, 4%, 6%, . . . , 98%, 100%.

Figure 3:
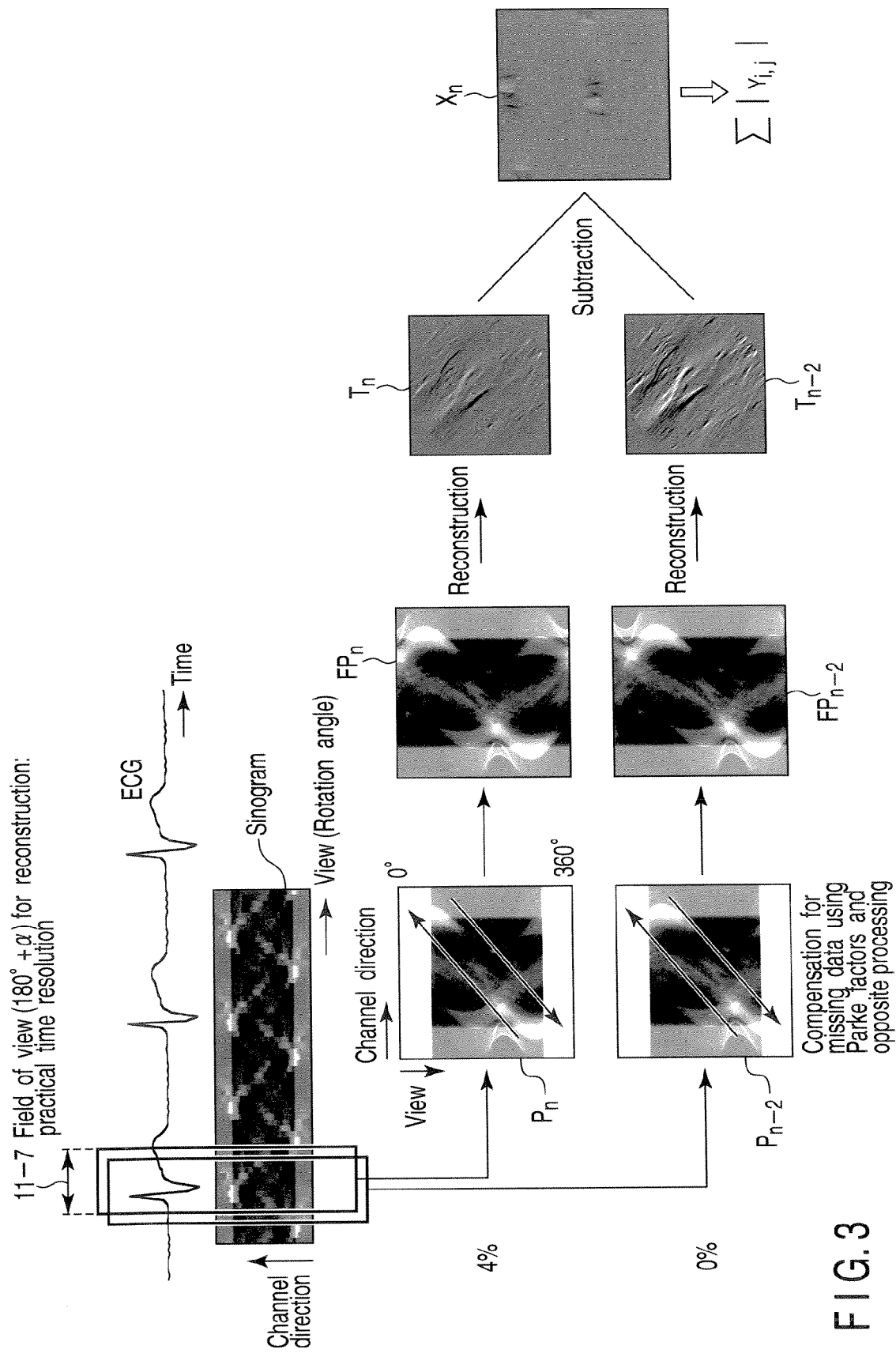
FIG. 3 is a supplementary view for steps S13 to S17 in FIG. 2.

The image reconstruction processing unit 206 reads out a projection data set corresponding to (180°+α) centered on a cardiac phase of 0% from the projection data storage unit 203 under the control of the system control unit 212 (S13). In other words, as shown in FIG. 3, a projection data set Pn corresponding to (180°+α) centered on a cardiac phase of 0% is extracted from the data (sonogram data) acquired by scanning in step S11. Note that a projection data set is defined as a set of projection data necessary for the reconstruction of one image, and is projection data in an angle range of (180°+α) centered on a specific phase in the half reconstruction method, as described above. On the other hand, in the full reconstruction method, a projection data set is projection data in an angle range of (360°) centered on a specific phase. This embodiment will exemplify a case wherein data corresponding to one cardiac period is extracted. However, projection data for the generation of one image may be formed by combining projection data in a plurality of different cardiac periods corresponding to the cardiac phase.

The projection data set Pn is used for half reconstruction, and hence partly lacks data. The image reconstruction processing unit 206 generates a full projection data set FPn corresponding to 360° by filtering the projection data set Pn with a two-dimensional filter (to be simply referred to as a filter hereinafter) using a so-called Parker's two-dimensional weighting factor map by using a general technique (S14).

The image reconstruction processing unit 206 generates an image (tomogram) on the basis of the full projection data set FPn (S15). The data of the image (tomogram) Tn is stored in the image storage unit 209. Note that the thickness of an image in the slice direction can be arbitrarily changed. The above processing may be performed after a plurality of images adjacent to each other in the slice direction are added in accordance with a designated thickness to form an image corresponding to the thickness.

It is obvious that a reconstructed image in this optimal phase determination processing is smaller in matrix size than a reconstructed image for actual diagnosis which is generated in accordance with the optimal phase determined in this processing. That the matrix size is small means that the resolution is low when an entire imaging FOV is set as a reconstruction FOV, or that a partial region to be described later (a region of interest ROI) of an imaging FOV is enlarged/reconstructed (zooming reconstruction) as a reconstruction FOV while the resolution remains the same.

The optimal phase determination unit 207 generates a subtraction image Xn by subtracting the data of an image Tn−2 which is two phases preceding the image Tn from the data of the image Tn stored in the image storage unit 209 (S16). In this case, since a projection data set is extracted at 2% intervals to reconstruct an image, images with a phase difference of 4% are subtracted from each other (see FIGS. 4B and 4C). In order to accurately determine an optimal phase with maximum precision, it is necessary to reconstruct an image with a high time resolution (at short intervals) of 1 to 2%. On the other hand, in order to elicit the movement of the heart to some extent, a phase difference of 3 to 6% more preferably 4 to 5% is required. Reconstructing an image at 2% intervals and setting a difference to two frames make it possible to satisfy both requirements, i.e., obtaining a high time resolution and eliciting the movement of the heart to some extent. Obviously, it suffices even if an image is reconstructed with a time resolution of 4% and a difference is obtained between two adjacent frames. In this case, although the time resolution decreases to half of a time resolution of 2%, the movement of the heart can be elicited to some extent. The operator should arbitrarily determine, in accordance with the heart rate of the subject, how to combine an image reconstruction interval and a difference interval.

The sum total of the absolute values of all the pixels constituting the subtraction image Xn generated in step S16 is calculated as an index value indicating the movement amount of the heart by the optimal phase determination unit 207. Note that an index value to be used is not limited to the sum total of the absolute values of all the pixels constituting the subtraction image Xn, and the sum total of the absolute values of a plurality of pixels in a partial region (local region) of the subtraction image Xn, typically a region of interest including the coronary artery designated on an image by the operator. In addition, the sum of squares may be used instead of the simple sum total of absolute values.

Figure 4:
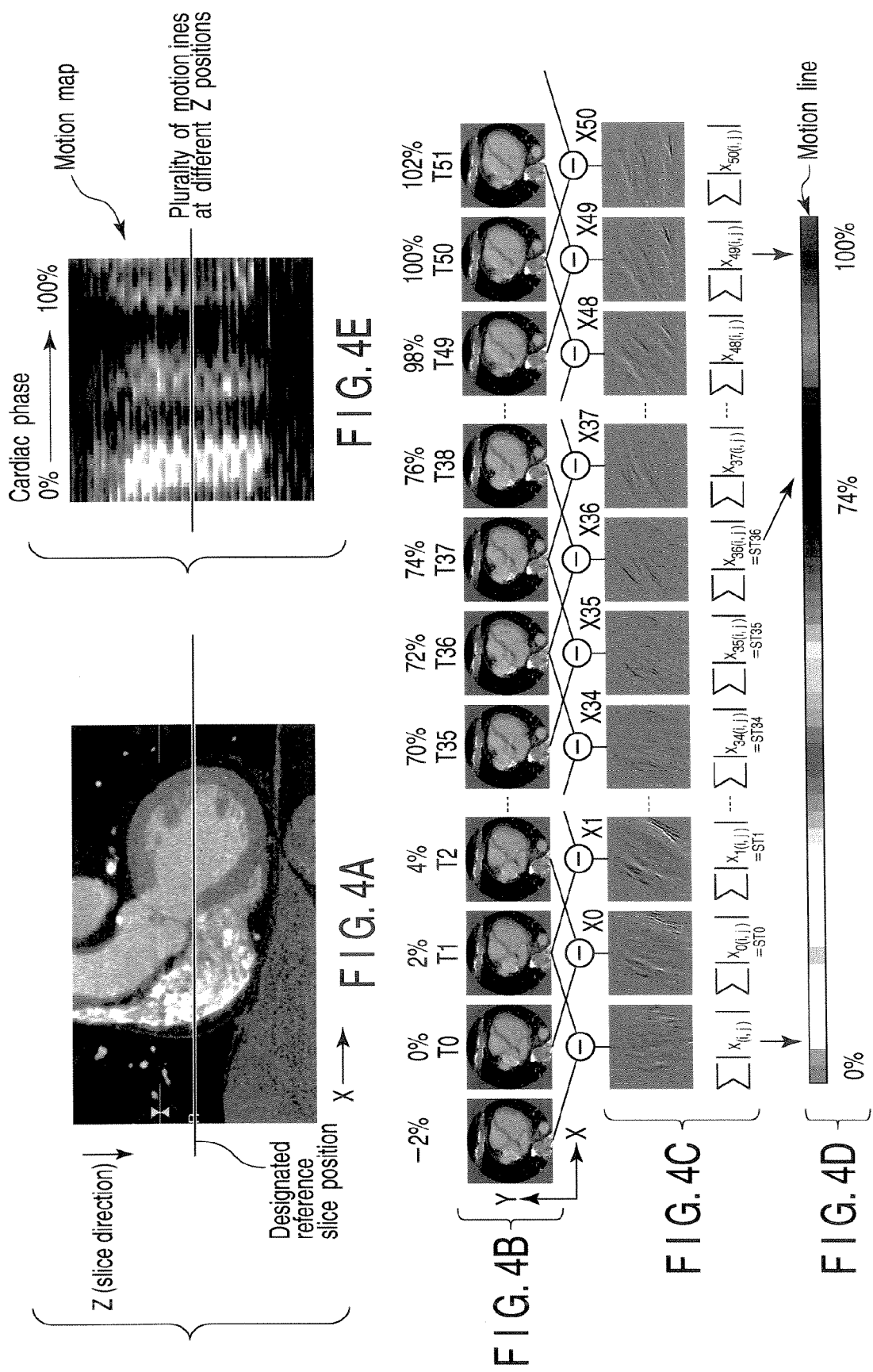
FIGS. 4A to 4E are detailed supplementary views for steps S13 to S19 in FIG. 2.

The series of processing in steps S13 to S17 is repeated through steps S18 and S19 until the variable n reaches the final value (50) in a cardiac period. With this operation, as shown in FIGS. 4A to 4E, 51 subtraction images X0 to X50 are obtained at 2% intervals in one cardiac period, and absolute value sum totals ST0 to ST50 are obtained from the respective subtraction images X0 to X50. FIG. 4A shows a CT tomogram along the slice direction. FIG. 4B shows a CT tomogram in each phase. FIG. 4C shows formulae for obtaining a subtraction image between CT tomograms corresponding to two phases and the sum (movement amount) of the pixel values of the subtraction image. FIG. 4D shows a motion line image representing the values of the movement amounts in the respective phases by changing the shading or color of the image in accordance with the values of the movement amounts. FIG. 4E shows a motion map image indicating a plurality of motion lines corresponding to the respective slice positions in correspondence with the slice positions.

Figure 5:
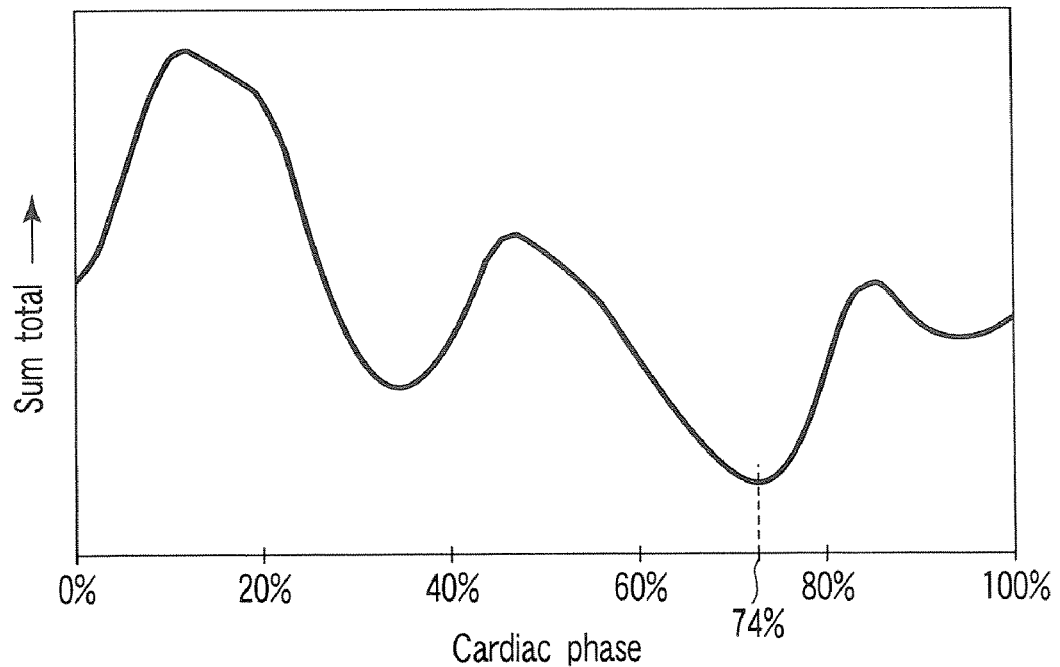
FIG. 5 is a graph showing an example of a temporal change in the absolute value sum total of subtraction images (a change in cardiac phase) for a supplementary explanation of step S20 in FIG. 2.
Figure 6:
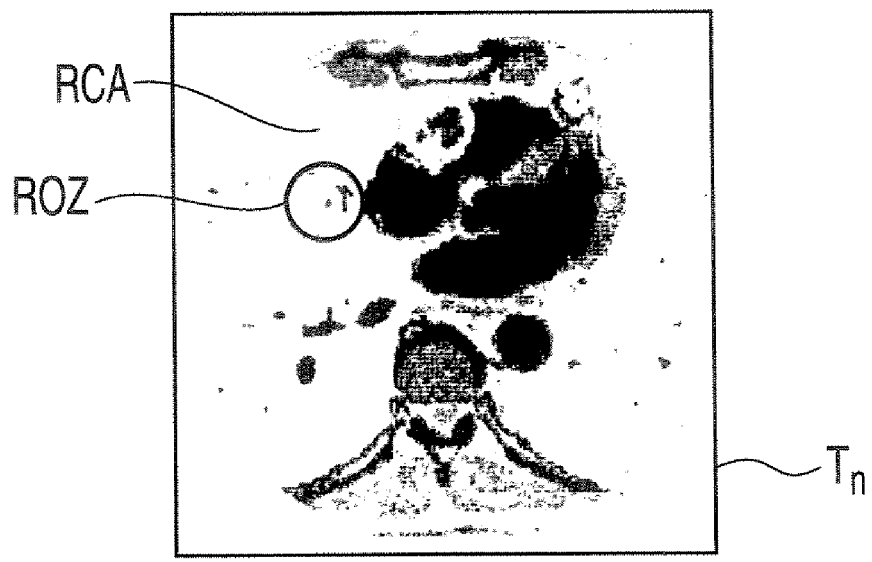
FIG. 6 is a view showing an example of localizing a processing range to a region of interest (coronary artery) in the first mode in this embodiment.
Figure 7:
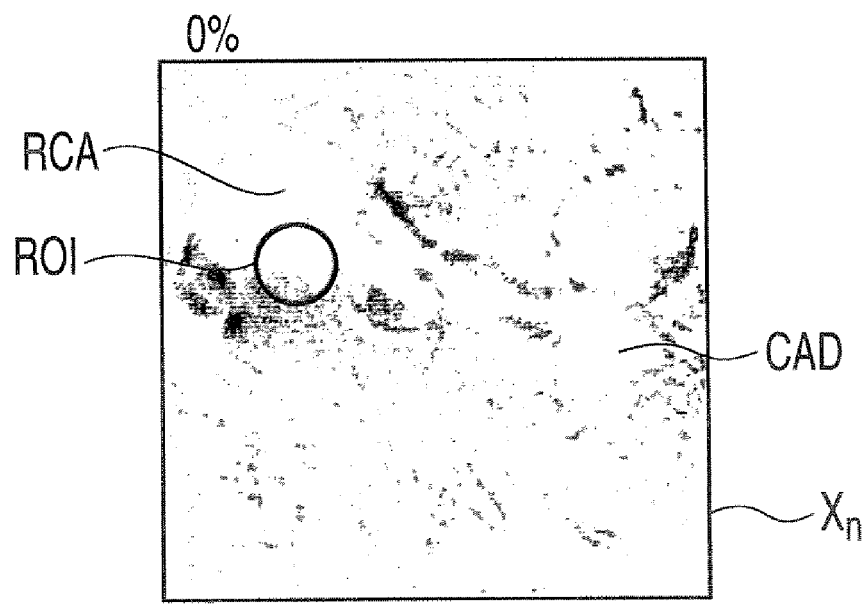
FIG. 7 is a view showing the region of interest in FIG. 6 on a subtraction image.

FIG. 5 shows changes in the absolute value sum totals ST0 to ST50 with time. The optimal phase determination unit 207 causes the display unit 210 to display the changes with time on the basis of the absolute value sum totals ST0 to ST50. Alternatively, information about temporal changes in the absolute value sum totals of pixels values in a region of interest shown in FIGS. 6 and 7 may be generated, and may be displayed on the display unit 210 as shown in FIG. 8.

The optimal phase determination unit 207 selects a single absolute value sum total corresponding to a state wherein the movement of the heart is minimum from the absolute value sum totals ST0 to ST50 (S20). In this case, the optimal phase determination unit 207 selects a minimum absolute value sum total STm. The minimum absolute value sum total STm originates from the image Tm and the image Tm−2, and indicates that the movement of the heart from a cardiac phase of (2×(m−2))% to a cardiac phase of (2×(m))% in one cardiac cycle is minimum or nearest to the minimum. The optimal phase determination unit 207 determines, for example, {(2×(m−2))%+(2×m)%}/2 as an optimal cardiac phase (S21). However, an optimal cardiac phase is not limited to this, and the optimal phase determination unit 207 may determine (2×(m−2))% as an optimal phase or may determine (2×m)%}/2 as an optimal phase.

Figure 8:
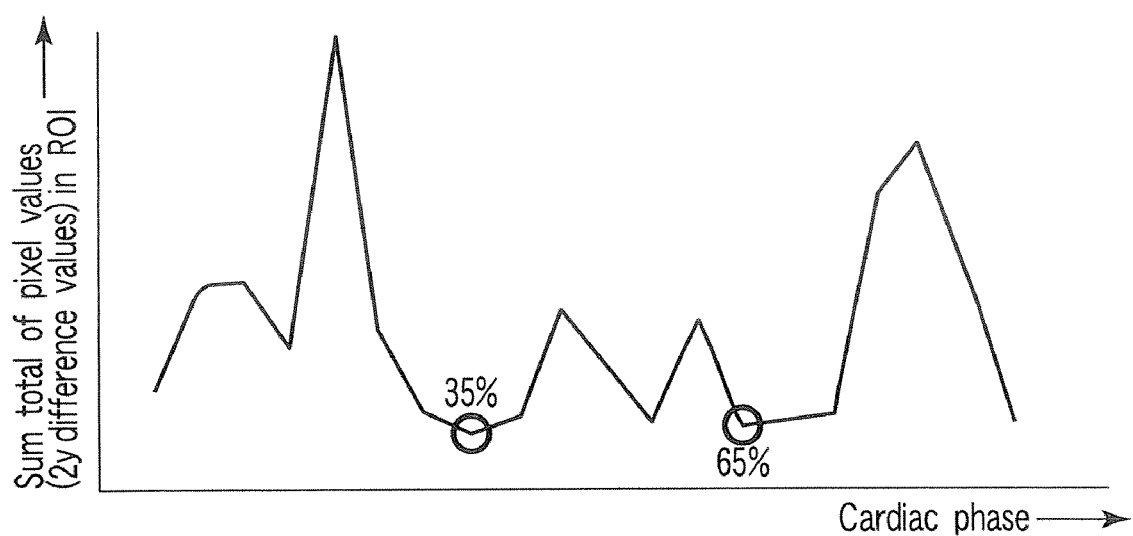
FIG. 8 is a graph showing a temporal change in the absolute value sum total (a change in cardiac phase) of subtraction image pixel values in the region of interest in FIG. 7.

Alternatively, the operator may manually designate a cardiac phase which he/she regards as optimal through an input unit from temporal changes in absolute value sum total displayed on the display unit 210 shown in FIG. 5 or 8.

The cardiac phase determined as an optimal phase in this manner is used in the main ECG-gated reconstruction method in the system control unit 212. CT tomograms of a plurality of slices corresponding to the determined cardiac phase are reconstructed, and an image can be displayed on the basis of the resultant three-dimensional image data.

Figure 9:
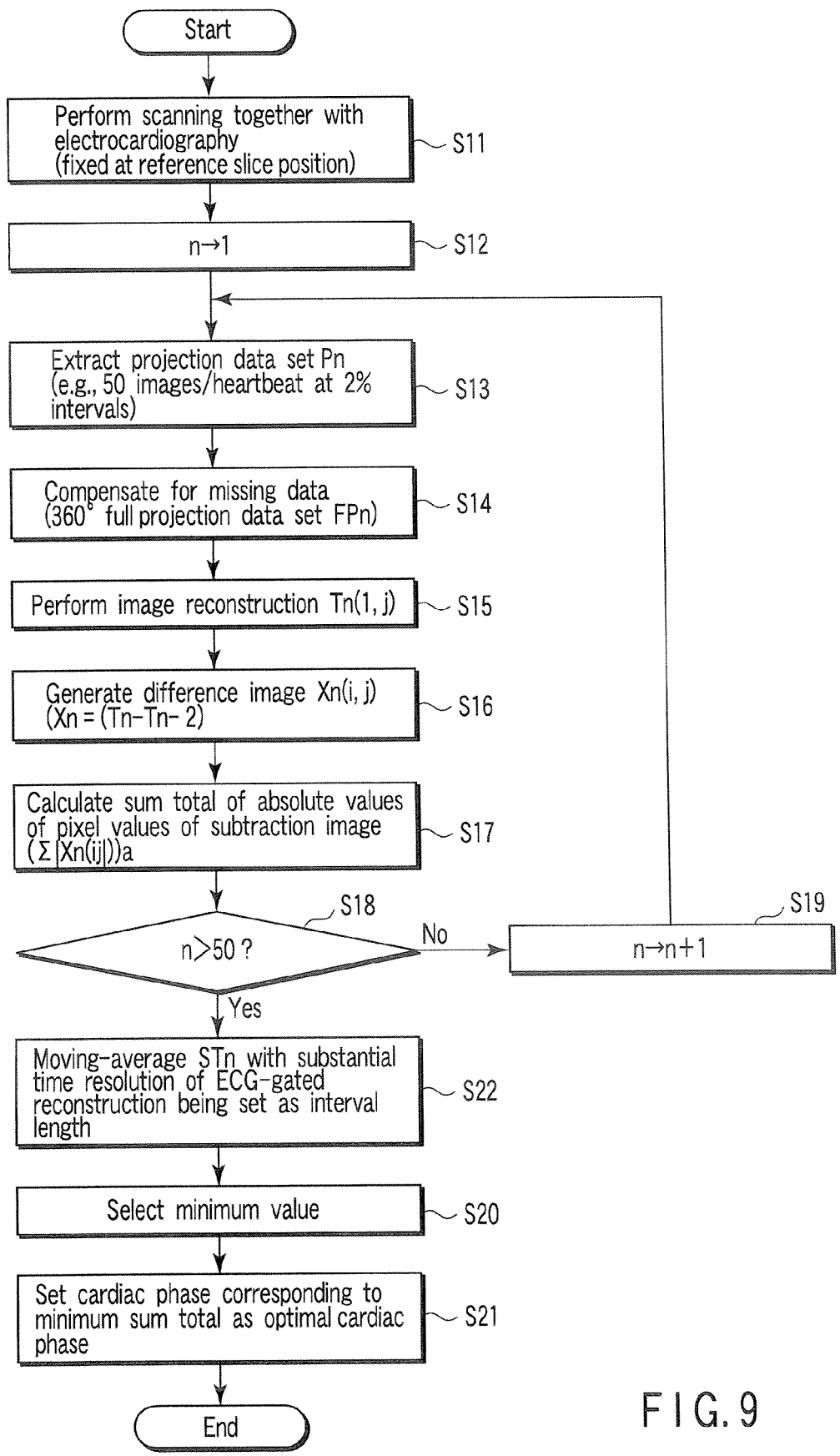
FIG. 9 is a flowchart showing a modification of the first mode in FIG. 2.

In the first mode described above, the minimum sum total STn of the pixel absolute values of the subtraction image Xn calculated in step S17 is selected. However, as shown in FIG. 9, a movement average throughout a proper interval length may be obtained with respect to the changes in absolute value sum total STn with time (FIG. 5) (S22), and the minimum value of the movement average may be determined as an optimal cardiac phase. As an interval length, a substantial time resolution in the half electrocardiogram reconstruction method is preferably set. Typically, the interval length of the movement average is set to the time length of a projection data set corresponding to (180°+α).

The second mode will be described next. As described above, in the first mode, an image is reconstructed from a projection data set (see FIG. 12A). In the second mode, pre-processing is performed without reconstruction of any image, and an optimal phase is determined from the projection data (raw data) which has not undergone reconstruction processing.

Figure 10:
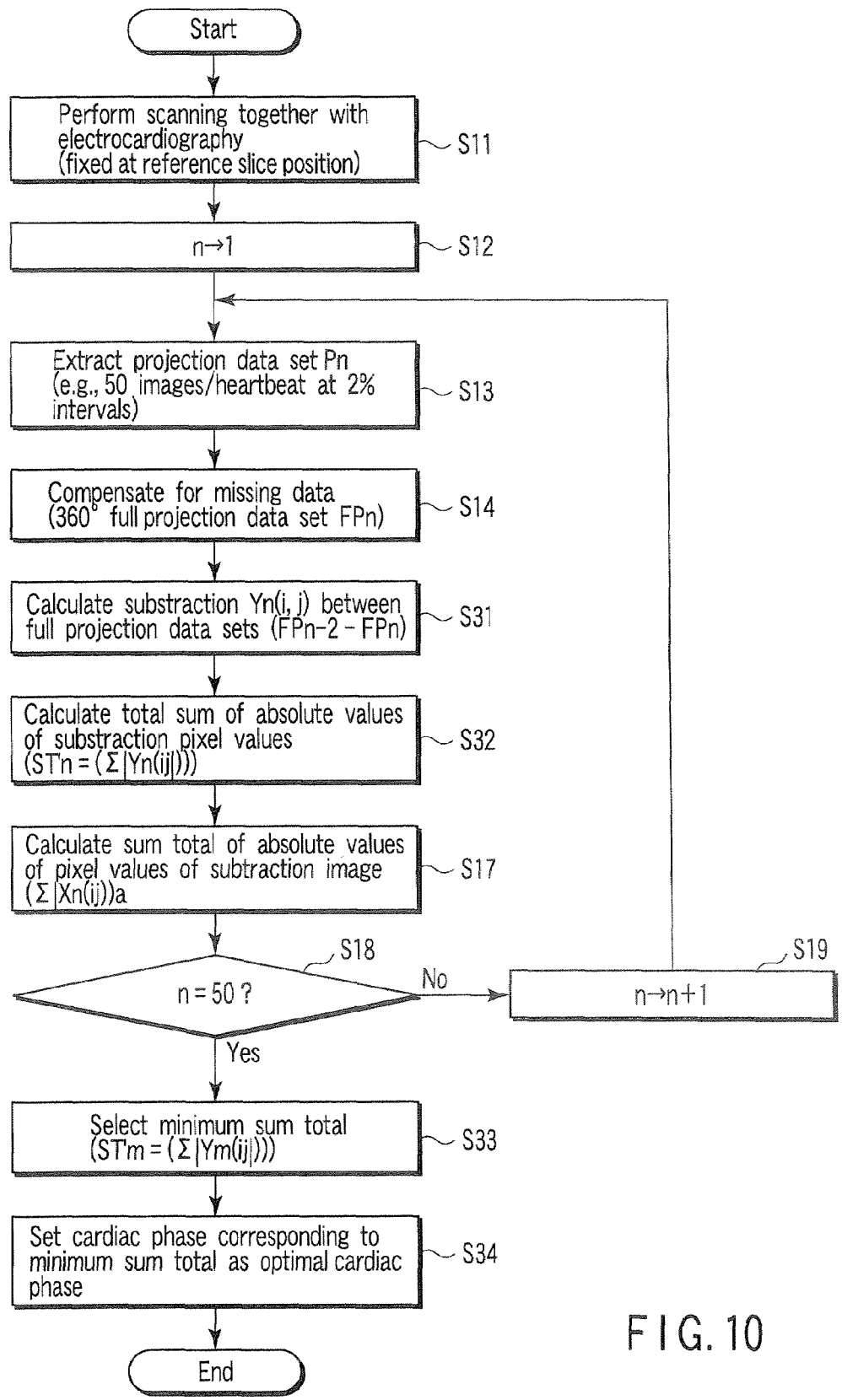
FIG. 10 is a flowchart showing an optimal cardiac phase determination sequence based on the second mode (raw data differences) in this embodiment.

FIG. 10 shows an optimal phase determination sequence in the second mode. The same step numbers as in FIG. 2 denote the same steps in FIG. 10, and a description thereof will be omitted. The 360° projection data set FPn generated in step S14 is stored in the image storage unit 209.

The optimal phase determination unit 207 generates a plurality of projection data sets necessary for the reconstruction of one image from the projection data stored in the image storage unit 209, obtains the differences between the respective projection data in the projection data sets, and obtains a projection data set as a set of the subtraction projection data. In this case, the 360° projection data set FPn and a projection data set FPn−2 which is two phases preceding the data set FPn are generated, and projection data with the same views (rotation angles) and channels are subtracted from each other, thereby generating a different projection data set Yn (S31).

Figure 11:
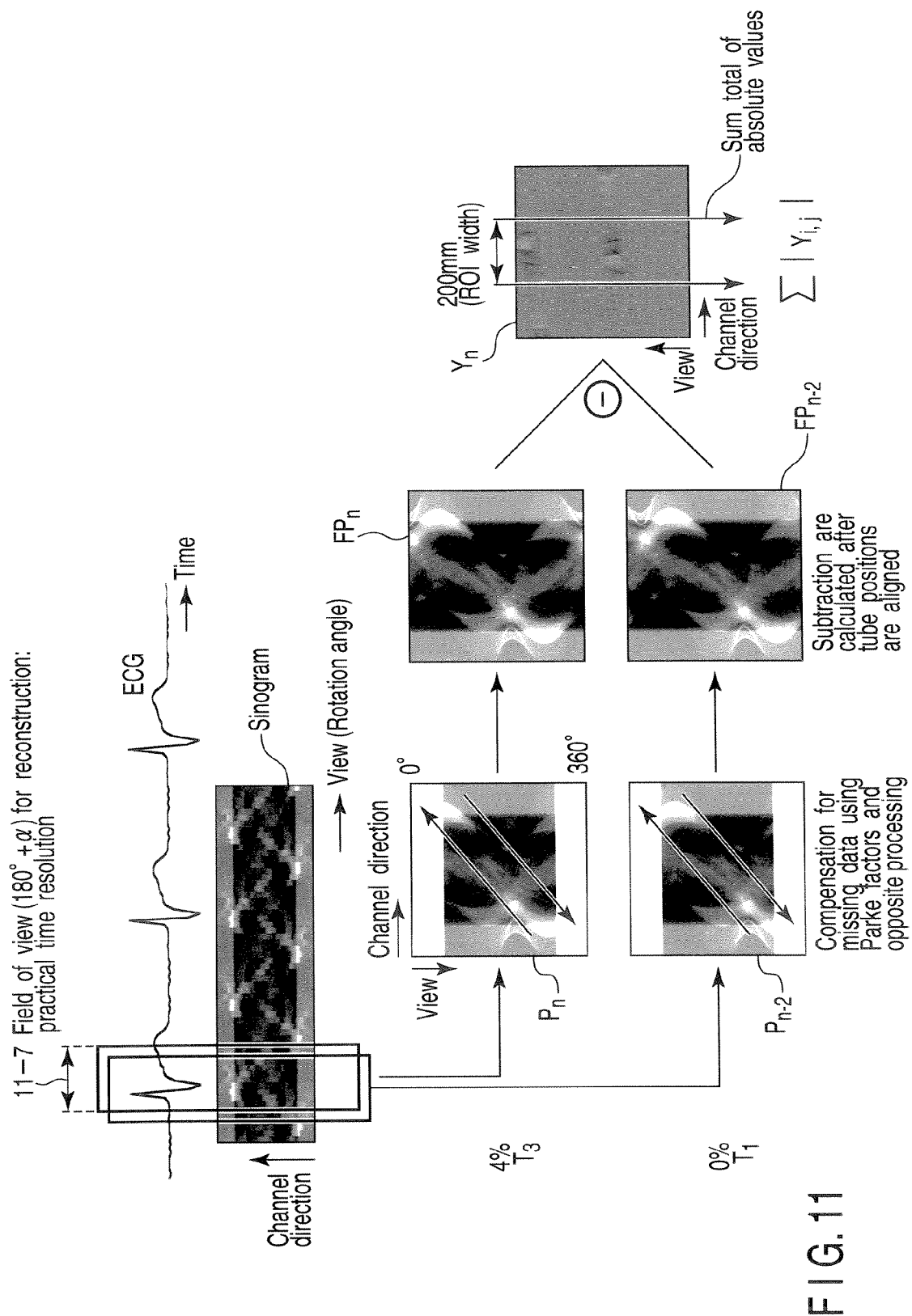
FIG. 11 is a view for explaining steps S13, S14, S31, and S32 in FIG. 10.

The sum total of the absolute values of the values of all the subtraction projection data (subtraction projection data corresponding to the respective views and the respective channel numbers) constituting the subtraction projection data set Yn generated in step S31 is calculated by the optimal phase determination unit 207 as an index value indicating the movement of the heart (S33). Note that an index value to be used is not limited to the sum total of the absolute values of the values of the subtraction projection data constituting the subtraction projection data set Yn, and a value representing a movement amount may be obtained by another method. For example, a sum total may be calculated upon localization to a width region (a region with, for example, a width of 200 mm in FIG. 11) corresponding to the region of interest ROI. In addition, the sum of squares may be used instead of the simple sum total of absolute values.

The optimal phase determination unit 207 selects a single absolute value sum total ST'm corresponding to a state wherein the movement of the heart is minimum from absolute value sum totals ST'0 to ST'50 (S33). In this case, the optimal phase determination unit 207 selects a minimum absolute value sum total ST'm. The minimum absolute value sum total ST'm originates from projection data sets Pm and Pm−2, and indicates that the movement of the heart from a cardiac phase of (2×(m−2))% to a cardiac phase of (2×(m))% in one cardiac cycle is minimum or nearest to the minimum. The optimal phase determination unit 207 determines, for example, {(2×(m−2))%+(2×m)%}/2 as an optimal cardiac phase (S21). However, an optimal cardiac phase is not limited to this, and the optimal phase determination unit 207 may determine (2×(m−2))% as an optimal phase or may determine (2×m)%}/2 as an optimal phase.

Determining an optimal phase by processing for projection data before reconstruction processing instead of a reconstructed image makes it possible to greatly decrease the number of steps.

Note that in the second mode, as in step S22 in FIG. 9 in the first mode, the movement average of changes in the sum total ST'n with time is obtained in an internal length, and the minimum value of the movement average value is determined as an optimal phase.

Figure 12:
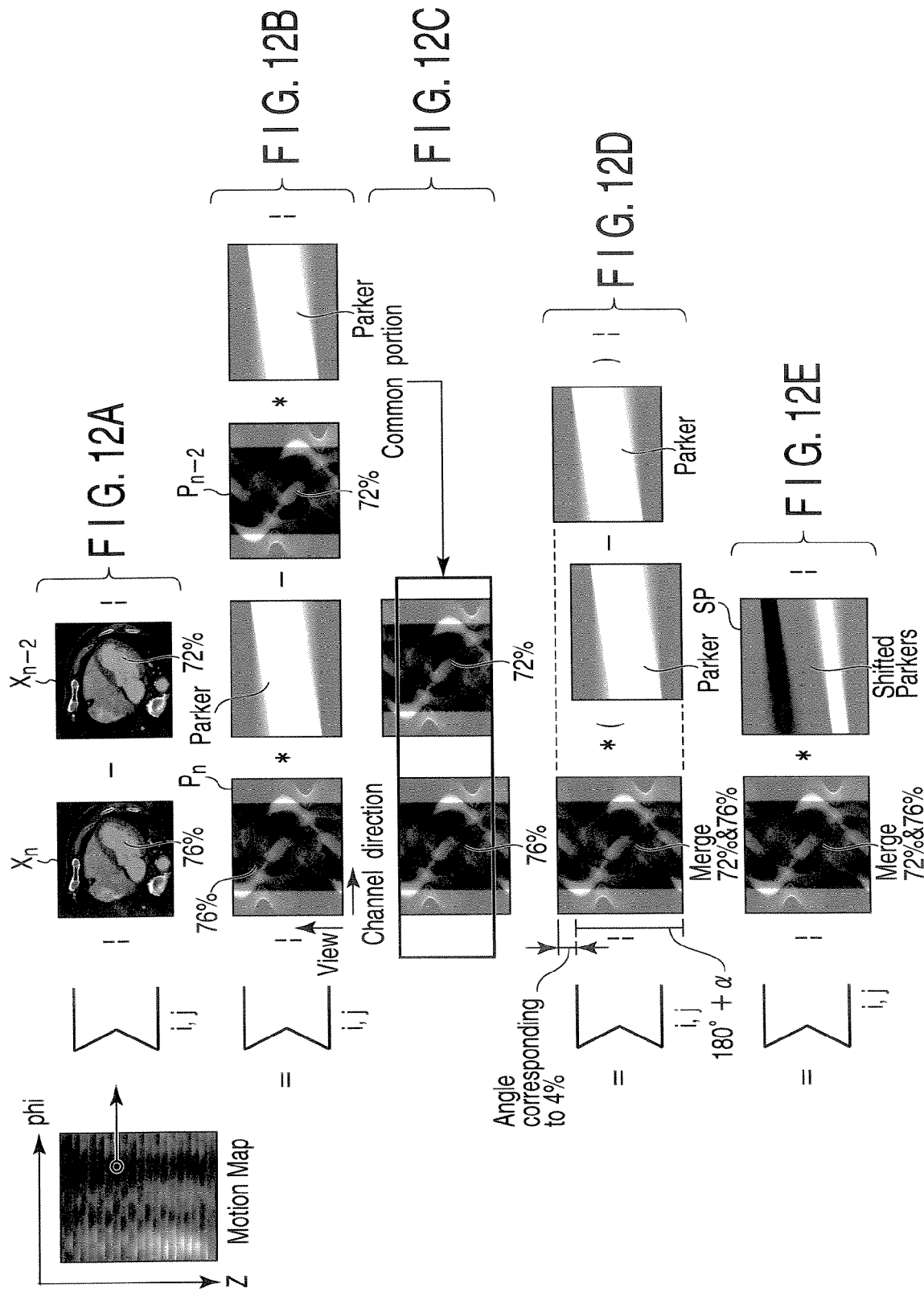
FIGS. 12A to 12E are views for explaining another processing in the second mode in this embodiment.

The number of steps in the second mode can be further decreased. According to the above description, as shown in FIG. 12B, the 360° full projection data set FPn is generated by filtering the projection data set Pn with a two-dimensional filter using a so-called Parker's two-dimensional weighting factor map in accordance with the half reconstruction method. The full projection data set FPn and the full projection data set FPn−2, which are shifted from each other by a predetermined angle corresponding to a cardiac phase of 4%, are subtracted from each other. An angle corresponding to a cardiac phase of 4% is, for example, 7°. The shift angle between the half projection data set Pn and the half projection data set Pn−2 is, for example, 7°, and is arbitrarily selected by the user from the range of 5 to 10°.

The present inventors therefore have focused on the fact that many portions of the half projection data set Pn and half projection data set Pn−2 which are shifted from each other by two phases are overlap, i.e., are identical data (see FIG. 12C). The Parker map corresponding to the half projection data set Pn and the phase-shifted (4%) Parker map corresponding to the half projection data set Pn−2 are subtracted from each other (FIG. 12D). Extended projection data sets which cover the angle range (180°+α+β; β is an angle corresponding to a cardiac phase of 4%) obtained by combining the half projection data set Pn and the half projection data set Pn−2 are filtered by using a difference Parker map SP obtained by shifting and subtraction (see FIG. 12E). The sum total of the filtered extended projection data sets is equal to the sum total shown in FIGS. 10 and 11.

According to this method, the number of times of data reading can be reduced to ½. In addition, performing subtraction processing on a Parker map in advance makes it possible to decrease the number of steps in filter processing to one. That is, according to this method, projection data corresponding to (180°+α)+{angle corresponding to phase difference (e.g., 4%) between subtraction targets} is read out, and the data is filtered with the single Parker map SP which have undergone shifting and subtraction in advance, thereby obtaining a result equivalent to that shown in FIGS. 2, 9, and 10.

Figure 13:
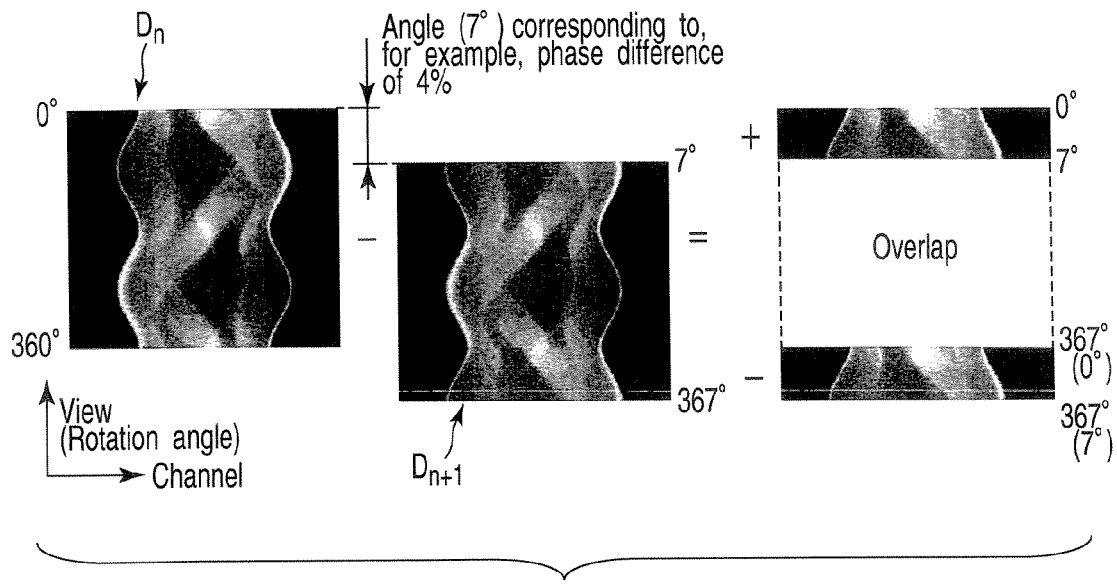
FIG. 13 is a view for explaining still another processing in the second mode in this embodiment.

The processing shown in FIG. 13 contributes to the speeding up of optimal phase determination processing. The control unit 212 causes the determination unit 207 to read out a plurality of full projection data sets D from the storage unit 203. Each projection data D covers the angle range of 360° required for the reconstruction of a one-frame image. A plurality of full projection data sets are shifted from each other by an angle corresponding to, for example, a phase difference of 4%. With this operation, most parts of a pair of adjacent full projection data sets Dn and Dn+1 overlap. A 4° front portion (corresponding to 0°--4°) of one full projection data set Dn does not overlap a rear portion (corresponding to 360° (0°)-364° (4°)) of the other full projection data set Dn+1 which is spaced apart from the data set Dn by 360°. The projection data set of one 4° (0°-4°) portion and the projection data set of the other 4° (360°-364°) portion, which do not overlap, are subtracted from each other while rotation angles (views) and channels are matched. The movement amount of the heart is calculated by calculating the absolute value sum total of difference values. This method does not include image reconstruction, and hence can greatly decrease the number steps.

Figure 14:
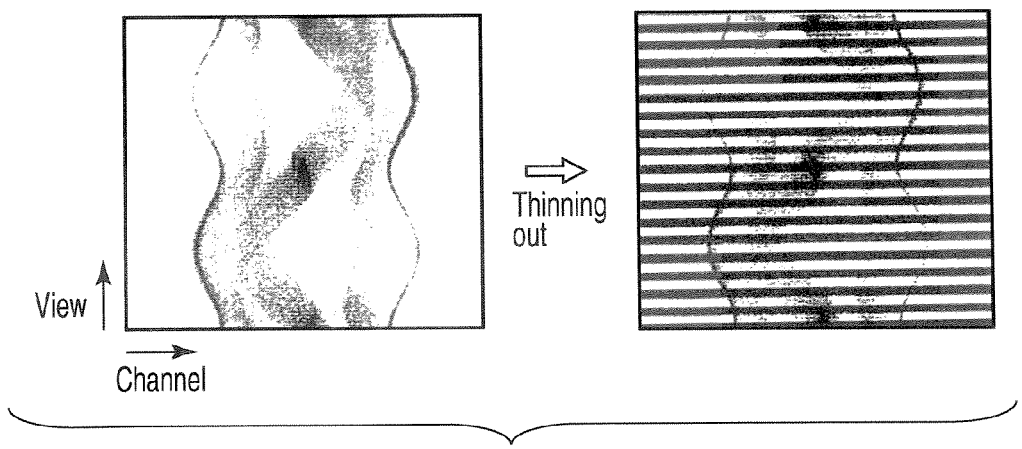
FIG. 14 is a view for explaining still another processing in the second mode in this embodiment.

In addition, for the speeding up of the processing, the half projection data set Pn may be partially thinned out, as shown in FIG. 14. Although the data set is typically thinned out on a view basis, it may be thinned out on a channel basis. Furthermore, the data set may be thinned out in association with views and channels.

Figure 15:
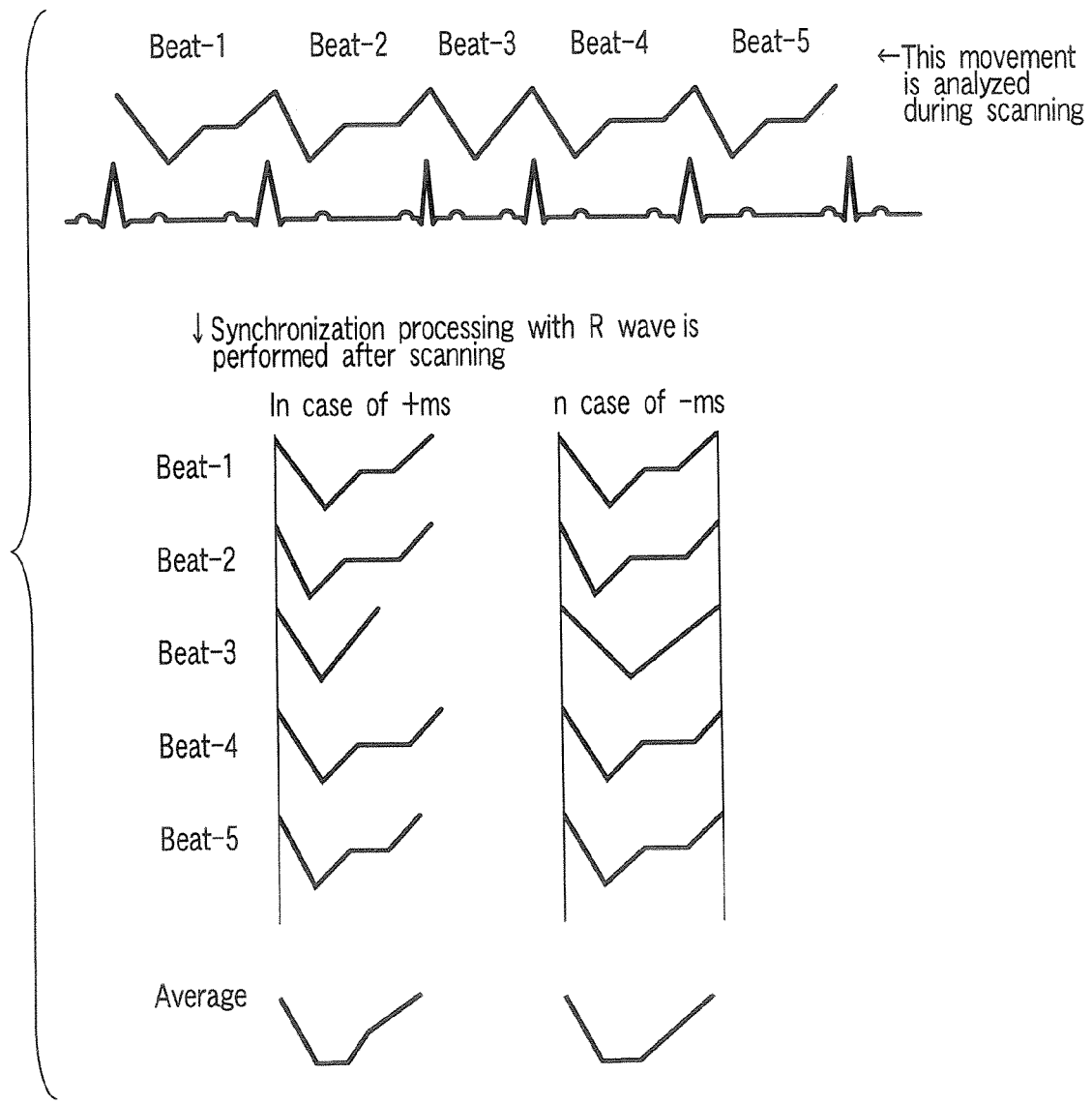
FIG. 15 is a view for explaining real-time processing in FIGS. 12A to 12E, 13, and 14.

Using the method in FIG. 12E or using it together with thinning processing makes it possible to sequentially calculate the sum totals (index values representing the movement amounts of the heart) of subtraction projection data Y instantaneously (dynamically) in parallel with the acquisition of the projection data during a scanning period for optimal phase determination, as shown in FIG. 15. Synchronization processing with an R wave is performed with respect to the sum total of the subtraction projection data Y after scanning. Since the calculation of an index value indicating the movement amount of the heart is complete at the same time as the end of scanning for optimal phase determination, an optimal cardiac phase can be determined in a short period of time after the end of the scanning operation. This method can improve the real-time performance when dynamic scanning is performed, in particular.

In the second mode described above, a movement amount is obtained on the basis of projection data before reconstruction. However, a movement amount with a predetermined thickness being given in the slice direction may be obtained by weighting/adding a plurality of projection data in the slice direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus, comprising:
an X-ray tube which generates X-rays;
an X-ray detector which detects X-rays transmitted through a subject to be examined;
a mechanism which continuously rotates the X-ray tube and the X-ray detector;
a storage unit which stores projection data detected by the X-ray detector;
a read unit configured to read out, from the projection data stored in the storage unit, a pair of partial projection data sets spaced apart from each other by 360°, each partial projection data set including a plurality of views;
an index generating unit which generates a plurality of indices indicating movement of a heart on the basis of a difference between the read out partial projection data sets;
a cardiac phase determination unit which determines a cardiac phase on the basis of the indices; and
a reconstruction unit which reconstructs an image on the basis of a full projection data set corresponding to the determined cardiac phase.

2. An apparatus according to claim 1, wherein the index generating unit calculates a sum total of the difference values as the index.

3. An apparatus according to claim 1, wherein the subtraction unit subtracts data with the same rotation angles and the same channel numbers from each other.

4. An apparatus according to claim 1, wherein the projection data is pre-processed data.

5. An apparatus according to claim 1, wherein the partial projection data sets cover an angle range selected from a range of 5 to 10°.

6. An apparatus according to claim 1, wherein the index generating unit is configured to moving average the indices along a time axis.

7. An apparatus according to claim 1, wherein the read unit reads out the partial projection data sets at intervals selected from a range of 2 to 6% of the cardiac phase.

8. An apparatus according to claim 1, wherein the read unit reads out the partial projection data sets at intervals of 2% of the cardiac phase.

9. An apparatus according to claim 1, wherein the index generating unit generates the index upon localization to part of each of the partial projection data sets.

10. An X-ray computed tomography apparatus comprising:
an X-ray tube which generates X-rays;
an X-ray detector which detects X-rays transmitted through a subject to be examined;
a mechanism which continuously rotates the X-ray tube and the X-ray detector;
a storage unit which stores projection data detected by the X-ray detector;
a read unit configured to read out from the stored projection data a plurality of extended half projection data sets which cover an angle range obtained by extending an angle (180°+α) required for half reconstruction by a predetermined angle (β);
a filter unit which filters the extended half projection data sets with a difference filter map obtained from a difference between a filter map for converting the half projection data sets in the angle range required for the half reconstruction into full projection data sets which cover 360° and a filter map shifted by the predetermined angle (β);
an index generating unit which generates a plurality of indices indicating movement of a heart on the basis of the filtered extended half projection data sets;
a cardiac phase determination unit which determines a cardiac phase on the basis of the indices; and
a reconstruction unit which reconstructs an image on the basis of a full projection data set corresponding to the determined cardiac phase.

11. An apparatus according to claim 10, wherein the index generating unit calculates a sum total of the filtered extended half projection data sets as the index.

12. An apparatus according to claim 10, wherein the filter unit thins out and filters part of the extended half projection data set.

13. An apparatus according to claim 10, wherein the projection data is pre-processed data.

14. An apparatus according to claim 10, further comprising a motion map generating unit which generates a motion map by arranging said plurality of generated indices along a time axis, generating a plurality of motion line images corresponding to a plurality of slice positions, and arranging said plurality of motion line images along a slice axis.

15. An apparatus according to claim 10, wherein the predetermined angle ($\beta$) corresponds to 4% of the cardiac phase.

16. An X-ray computed tomography apparatus comprising:
   an X-ray tube which generates X-rays;
   an X-ray detector which detects X-rays transmitted through a subject to be examined;
   a mechanism which continuously rotates the X-ray tube and the X-ray detector;
   a storage unit which stores projection data detected by the X-ray detector;
   a generating unit configured to generate a plurality of subtraction images from a plurality of images with different cardiac phases which are reconstructed on the basis of the projection data;
   a calculation unit which calculates a plurality of indices indicating movement of a heart on the basis of said plurality of subtraction images;
   a cardiac phase determination unit which determines a cardiac phase on the basis of the indices; and
   a reconstruction unit which reconstructs an image on the basis of a projection data set corresponding to the determined cardiac phase.

17. An X-ray computed tomography apparatus comprising:
   an X-ray tube which generates X-rays;
   an X-ray detector which detects X-rays transmitted through a subject to be examined;
   a mechanism which continuously rotates the X-ray tube and the X-ray detector;
   a storage unit which stores projection data detected by the X-ray detector;
   a reconstruction unit which reconstructs a plurality of images with different cardiac phases on the basis of the projection data;
   a subtraction image generating unit which generates a plurality of subtraction images from said plurality of images;
   an index calculation unit which calculates a plurality of indices indicating movement of a heart from said plurality of subtraction images; and
   a display unit which displays a temporal change associated with the movement of the heart on the basis of the indices.

18. An X-ray computed tomography apparatus including an X-ray tube and an X-ray detector to acquire projection data of a subject to be examined, and generating an image of the subject on the basis of the projection data and cardiac information, the apparatus comprising:
   a calculation unit which calculates movement amounts on the basis of a non-overlap portion between a first projection data set required to generate an image corresponding to a first cardiac phase and a second projection data set required to generate an image corresponding to a second cardiac phase; and
   a cardiac phase determination unit which determines a specific cardiac phase on the basis of the movement amounts.

19. An X-ray computed tomography apparatus comprising:
   an X-ray tube which generates X-rays;
   an X-ray detector which detects X-rays transmitted through a subject to be examined;
   a mechanism which continuously rotates the X-ray tube and the X-ray detector;
   a storing unit which stores projection data detected by the X-ray detector;
   a weighting factor generating unit which generates weighting factors on the basis of differences between weights required for the half reconstruction and shifted weights;
   an index generating unit which generates indices indicating movement of a heart on the basis of the projection data weighted by the weighting factors;
   a cardiac phase determination unit which determines a cardiac phase on the basis of the indices; and
   a reconstruction unit which reconstructs an image on the basis of a projection data set corresponding to the determined cardiac phase.

* * * * *